United States Patent
Peng

(10) Patent No.: US 12,133,541 B2
(45) Date of Patent: Nov. 5, 2024

(54) FEED COMPOSITION COMPRISING HEXAHYDRO-β-ACID COMPONENT COMPOUNDS AND APPLICATION THEREOF

(71) Applicant: WISORIG TECHNOLOGIES PTE. LIMITED, Singapore (SG)

(72) Inventor: Xianfeng Peng, Guangzhou (CN)

(73) Assignee: WISORIG TECHNOLOGIES PTE. LIMITED, Singapore (SG)

( * ) Notice: Subject to any disclaimer, the term of this patent is extended or adjusted under 35 U.S.C. 154(b) by 462 days.

(21) Appl. No.: 17/612,579

(22) PCT Filed: May 23, 2019

(86) PCT No.: PCT/CN2019/088053
§ 371 (c)(1),
(2) Date: Nov. 19, 2021

(87) PCT Pub. No.: WO2020/232689
PCT Pub. Date: Nov. 26, 2020

(65) Prior Publication Data
US 2022/0232856 A1    Jul. 28, 2022

(51) Int. Cl.
A23K 20/105     (2016.01)

(52) U.S. Cl.
CPC .................. *A23K 20/105* (2016.05)

(58) Field of Classification Search
CPC ....... A23K 20/105; A23K 50/00; A23K 40/30
See application file for complete search history.

(56) References Cited

U.S. PATENT DOCUMENTS

| 8,969,419 B2 * | 3/2015 | Garden ............ A23K 50/10 514/689 |
| 2009/0263522 A1 | 10/2009 | Babish et al. |
| 2016/0368853 A1 | 12/2016 | Peng et al. |

FOREIGN PATENT DOCUMENTS

| CN | 104710307 A | 6/2015 |
| CN | 105481893 A | 4/2016 |
| EP | 3098214 A1 | 11/2016 |
| WO | WO-2016131204 A1 * | 8/2016 ............ C07C 69/28 |

OTHER PUBLICATIONS

Peng X. et al. WO 2016131204-A, Machine Translation, English, Aug. 25, 2026, pp. 1-4 (Year: 2016).*
Yumei Liu, "Synthesis, characterization, crystal structure, a-nd antioxidant activity of hexahydro-β-acids", Journal of Molecular Structure, vol. 1175, p. 721-727, date Aug. 11, 2018.
European Search Report, dated Jun. 8, 2022.
International Search Report of PCT/CN2019/088053, dated Feb. 28, 2020.
English Translation of International Search Report of PCT/CN2019/088053.
English Translation of CN105481893A.
English Translation of CN104710307A.

* cited by examiner

*Primary Examiner* — Hong T Yoo
(74) *Attorney, Agent, or Firm* — Kam Wah Law

(57) ABSTRACT

A feed composition comprising hexahydro-β-acid component compounds shown in formula I, i.e. hexahydrocolupulone and/or hexahydroadlupulone, applications of the feed composition and the hexahydro-β-acid component compounds, and a method for using the feed composition to improve animal production performance.

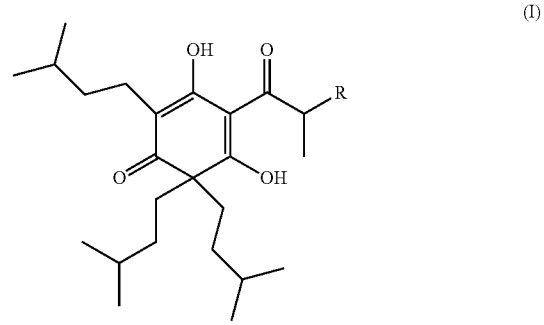

(I)

14 Claims, No Drawings

FEED COMPOSITION COMPRISING HEXAHYDRO-β-ACID COMPONENT COMPOUNDS AND APPLICATION THEREOF

CROSS REFERENCE TO RELATED APPLICATION

This is a U.S. national stage application of the International Patent Application No. PCT/CN2019/088053, filed May 23, 2019, which is incorporated herein by reference in its entirety.

TECHNICAL FIELD

The present invention relates to the field of animal feed additives, and particularly relates to a feed composition comprising hexahydro-β-acid compounds and the use thereof.

BACKGROUND

Hop acids are organic acids derived from hops, including α-acids and β-acids, which can be used as antibiotic alternatives in animal feeds with their biological performance of sterilization, antibacterial activity or regulating metabolites. Among these acids, β-acids have higher antibacterial activity. Due to the poor stability and solubility of hop acids, they were usually mixed to an animal feed after grinding, or sprayed and wrapped or mixed in/into an animal feed as a 1% aqueous solution of their potassium salts, which were inconvenient for their use in animal breeding. Some studies proposed that dihydrogenated, tetrahydrogenated, or hexahydrogenated derivatives of hop acids exhibited changes in activity, stability, solubility, or other properties. However, unfortunately, it was soon reported that, hexahydrogenated β-acids and metallic salts thereof (referred to as hexahydro-β-acids) were unstable to heat. In addition, when they were mixed in feed and stored at room temperature, hexahydro-β-acids would degrade rapidly resulting in a decrease in the concentration of hexahydro-β-acids, and could not satisfy the requirements as a feed additive.

In view of the above, the present application is proposed.

SUMMARY

The objects of the present application comprise providing a feed composition, wherein the feed composition comprises an optional feed-acceptable adjuvant; and at least one compound selected from hexahydro-β-acid compounds represented by formula (I) and feed-acceptable salts thereof.

The objects of the present application also comprise providing the use of the feed composition and hexahydro-β-acid compounds in the preparation of animal feed additives for improving animal production performance.

The objects of the present application also comprise providing the use of the feed composition and hexahydro-β-acid compounds and feed-acceptable salts thereof in the preparation of animal feeds.

The objects of the present application also comprise providing a method for improving animal production performance.

To achieve at least one of the objects of the present application, the following technical solutions are proposed.

In one aspect, the present application provides a feed composition, wherein the feed composition comprises an optional feed-acceptable adjuvant; and at least one compound selected from hexahydro-β-acid compounds represented by formula (I) and feed-acceptable salts thereof;

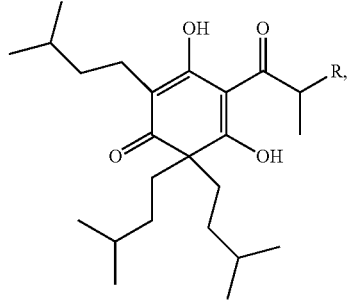

(I)

wherein R is methyl or ethyl, and wherein the feed composition is free of hexahydro-lupulone or a salt thereof.

In another aspect, the present application also provides the use of the feed composition in the preparation of animal feed additives for improving animal production performance.

In another aspect, the present application also provides the use of a hexahydro-β-acid compound or a feed-acceptable salt thereof in preparation of animal feed additives for improving animal production performance, wherein the hexahydro-β-acid compound is at least one of the compounds represented by formula (I):

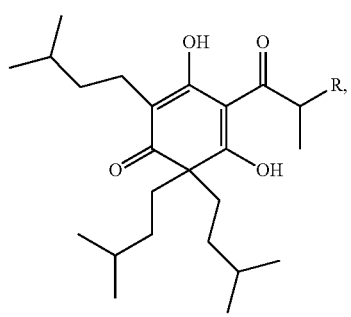

(I)

wherein R is methyl or ethyl.

In another aspect, the present application also provides the use of the feed composition in the preparation of animal feeds.

In another aspect, the present application also provides the use of a hexahydro-β-acid compound or a feed-acceptable salt thereof in the preparation of animal feeds, wherein the hexahydro-β-acid compound is at least one of the compounds represented by formula (I):

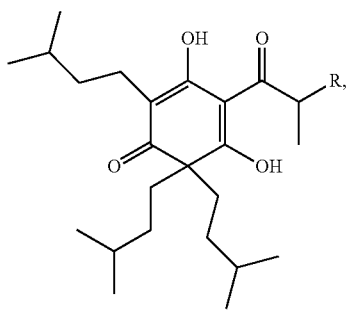

(I)

wherein R is methyl or ethyl.

In another aspect, the present application also provides a method for improving animal production performance, comprising: feeding an animal with the feed composition of the present application, or feeding an animal with a feed comprising the feed composition of the present application.

Compared with prior art, the present application comprises for example the following beneficial effects:

In the present application, it has been discovered that, in the group of the three main types of hexahydro-β-acids, hexahydro-colupulone, hexahydro-adlupulone, and hexahydro-lupulone, which are the three main components of hexahydro-β-acids, hexahydro-lupulone exhibit very poor stability in feeds, which is the major factor leading to the decline in stability of hexahydro-β-acids in feeds. Moreover, in the present application, it has been discovered that, each of hexahydro-colupulone and hexahydro-adlupulone, when separately added in feeds, exhibits favourable stability in stability testing at ambient temperature, and an effect on animal production performance similar to that of hexahydro-β-acids in an animal breeding testing, wherein the effect of hexahydro-colupulone on animal production performance is better than that of hexahydro-β-acids. Furthermore, in the present application, it has been discovered that the combination of hexahydro-colupulone and hexahydro-adlupulone in feeds is more effective than hexahydro-β-acids in the breeding testing.

Any embodiment of any aspect of the present application can be combined with other embodiments as long as there is no contradiction therebetween. Moreover, any technical feature in any embodiment of any aspect of the present application can be applied as the same technical feature in other embodiments, as long as there is no contradiction therebetween.

DETAILED DESCRIPTION OF THE EMBODIMENTS

The foregoing content only outlines certain aspects of the present application, which is however not limited to these aspects. The content involved above and in other aspects will be described in more detail and complete as below.

A further detailed description of the present application is given below.

Herein certain embodiments of the present application will be described in detail, examples of which are illustrated by the accompanying structural formulas and chemical formulas. The intention of the present application covers all substituted, modified, and equivalent technical solutions, which all fall within in the scope of the present application as defined by the claims. In addition, certain technical features of the present application, in order to be clearly present, may be described separately in multiple independent embodiments; however, they can also be provided, in a single embodiment, in combination or in any suitable sub-combination.

Feed Compositions Involved in the Present Application

A stable feed composition comprises an optional feed-acceptable adjuvant; and at least one compound selected from hexahydro-β-acids compounds represented by formula (I) and feed-acceptable salts thereof, wherein the feed-acceptable adjuvant is a carrier, a diluent, a excipient and a dissolvent, or a combination thereof.

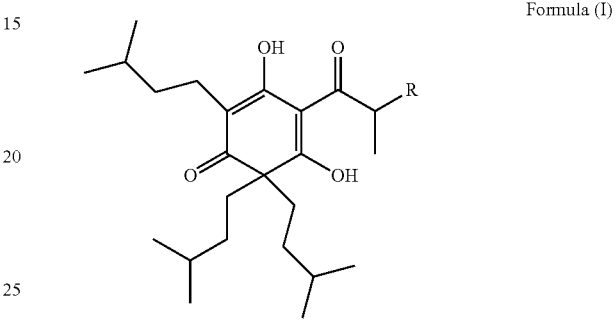

Formula (I)

In formula (I), R is methyl or ethyl. When R is methyl, the hexahydro-β-acid compound represented by formula (I) is hexahydro-colupulone; when R is ethyl, the hexahydro-β-acid compound represented by formula (I) is hexahydro-adlupulone.

The hexahydro-β-acid compounds represented by formula (I) have asymmetric centers and can exist as a meso compound, a racemate, a stereoisomer, a geometric isomer, a tautomer, a single enantiomer, a single diastereomer, and diastereomers, and it should be noted that these compound forms are included in the present application. The hexahydro-β-acid compounds can be obtained commercially or by chemists having ordinary skill through semi-synthesis from plant-sourced raw materials or through total-synthesis.

The "composition" involved herein refers to a collection of compounds comprising one or more compounds as active ingredients.

The terms "comprise," "include," "contain," "with" and variants thereof herein mean an open-ended expression, which includes the contents explicitly stated in the present application and does not exclude contents of other aspects. However it should be noted that the feed composition provided herein excludes hexahydro-lupulone or the salts or esters thereof. In one or more embodiments, in addition to the hexahydro-β-acid compounds represented by formula (I), other hexahydro-β-acid compounds are excluded (except for the unavoidable presence of the other hexahydro-β-acid compounds in tiny amounts as impurities).

The "stable feed composition" involved herein refers to a composition for animal consumption, which has sufficient stability to allow production, and in which the integrity of compounds can be maintain for a long enough period of time for the purpose described in detail in the present application.

The "feed-acceptable salt" refers to a salt formed by the hexahydro-β-acid compound of the present invention with an organic base, inorganic base, organic acid or inorganic acid, those are non-toxic to animals, or a salt formed with metal chlorides under alkaline conditions. The term "feed-acceptable" refers to that the substance or composition must be chemically or toxicologically suitable for and relevant to the resulting feed or fed animals.

The organic acids involved herein include but are not limited to acetic acid, maleic acid, succinic acid, mandelic acid, fumaric acid, malonic acid, malic acid, 2-hydroxypropionic acid, pyruvic acid, oxalic acid, glycolic acid, salicylic acid, glucuronic acid, galactonic acid, citric acid, tartaric acid, aspartic acid, glutamic acid, benzoic acid, p-toluic acid, cinnamic acid, p-toluenesulfonic acid, benzenesulfonic acid, methanesulfonic acid, ethanesulfonic acid, trifluoromethanesulfonic acid, or a combination thereof.

The inorganic acids involved herein include but are not limited to sulfuric acid, hydrochloric acid, hydrobromic acid, hydroiodic acid, and phosphoric acid.

The "feed-acceptable salts" involved herein can also be metal salts, which include but are not limited to sodium salt, potassium salt, calcium salt, magnesium salt, zinc salt, copper salt, manganese salt, cobalt salt, and iron salt.

The "carrier" involved herein refers to a feedable substance capable of carrying active ingredients, improving their dispersibility, and exhibiting favourable chemical stability and adsorption. The carriers are organic or inorganic carriers. Organic carriers are materials rich in crude fibers, including but not limited to corn flour, corn cob flour, wheat bran, rice husk flour, defatted rice bran, rice bran, corn stalk flour, and peanut husk flour. Inorganic carriers are minerals, mainly classified into calcium salts and silicon oxides and used for the production of trace element premixes, including but not limited to calcium carbonate, silicate, vermiculite, zeolite, and meerschaum.

The "diluent" involved herein refers to a substance that uniformly disperses the additive raw materials, and dilutes the high-concentration additive raw materials into low-concentration premixed agents or premixes, which separates trace components and reduces interactions between active ingredients, so as to increase the stability of the active ingredients without affecting the physical and chemical properties of involved substances. The diluent can be an organic diluent or inorganic diluent. Organic diluents include but are not limited to corn flour, degerminated corn flour, dextrose (glucose), sucrose, semolina with bran, fried soybean flour, secondary flour, and corn gluten meal. Inorganic diluents include but are not limited to limestone, calcium dihydrogen phosphate, shell powder, kaolin (white clay), table salt and sodium sulfate.

The excipients include one or more selected from the group consisting of wetting agents that induce the inherent viscosity of a substance, adhesives that bind the substances together, disintegrants that breaks the entire sheet of a substance into many fine particles, retention aids that reduces the friction between particles, and anti-adhesion agents that prevent material adhesion, including but not limited to magnesium stearate, talc, plant oils, magnesium lauryl sulfate, starch, starch slurry, water, inorganic salts, dextrin, and powdered sugar.

The "dissolvent" involved herein refers to a solvent required to dissolve or disperse solids, including but not limited to water, ethanol, and glycerin.

In some embodiments, the hexahydro-β-acid compound represented by formula (I) included in the feed composition is hexahydro-colupulone or a feed-acceptable salt thereof, or hexahydro-adlupulone or a feed-acceptable salt thereof, or a combination of hexahydro-colupulone or a feed-acceptable salt thereof and hexahydro-adlupulone or a feed-acceptable salt thereof.

In one embodiment, the hexahydro-β-acid compound represented by formula (I) included in the feed composition is hexahydro-colupulone or a feed-acceptable salt thereof.

In one embodiment, the hexahydro-β-acid compound represented by formula (I) included in the feed composition is hexahydro-adlupulone or a feed-acceptable salt thereof.

In one embodiment, the hexahydro-β-acid compound represented by formula (I) included in the feed composition is a combination of hexahydro-colupulone or a feed-acceptable salt thereof and hexahydro-adlupulone or a feed-acceptable salt thereof.

In some embodiments, when the hexahydro-β-acid compound represented by formula (I) included in the feed composition is a combination of hexahydro-colupulone or a feed-acceptable salt thereof and hexahydro-adlupulone or a feed-acceptable salt thereof, wherein hexahydro-colupulone or a feed-acceptable salt thereof and hexahydro-adlupulone or a feed-acceptable salt thereof, are provided respectively at a weight unit of 1 and a weight unit of not higher than 0.5 and not lower than 0.01.

In some embodiments, when the hexahydro-β-acid compound represented by formula (I) included in the feed composition is a combination of hexahydro-colupulone or a feed-acceptable salt thereof and hexahydro-adlupulone or a feed-acceptable salt thereof, wherein hexahydro-colupulone or a feed-acceptable salt thereof and hexahydro-adlupulone or a feed-acceptable salt thereof, are provided respectively at a weight unit of 1 and a weight unit of 0.5.

In some embodiments, when the hexahydro-β-acid compound represented by formula (I) included in the feed composition is a combination of hexahydro-colupulone or a feed-acceptable salt thereof and hexahydro-adlupulone or a feed-acceptable salt thereof, wherein hexahydro-colupulone or a feed-acceptable salt thereof and hexahydro-adlupulone or a feed-acceptable salt thereof, are provided respectively at a weight unit of 1 and a weight unit of 0.25.

In some embodiments, the hexahydro-β-acid compound included in the feed composition is provided as a coated substance suitable for feeds.

The term "coated substance" involved herein refers to a substance formed by coating the hexahydro-β-acid compound with a feed-acceptable adjuvant or a combination of multiple feed-acceptable adjuvants using specific devices in a specific process, for example, microcapsules manufactured by coating hexahydro-β-acid compounds with natural or synthetic feed-acceptable adjuvants, or matrix microspheres formed by dissolving and/or dispersing the hexahydro-β-acid compound in a feed-acceptable adjuvant or a combination of multiple feed-acceptable adjuvants.

Furthermore, the feed-acceptable adjuvants include natural polymer materials, semi-synthetic polymer materials, and synthetic polymer materials.

Particularly, the natural polymer materials as used herein include but are not limited to starch, alginates, chitosan, proteins, and gum arabic; the semi-synthetic polymer materials as used herein include but are not limited to fatty acids, fatty glycerides, fatty alcohols, cellulose acetate phthalate, ethyl cellulose, methyl cellulose, hydroxypropyl cellulose, and salts of carboxymethyl cellulose; the synthetic polymer materials as used herein include but are not limited to polyvinylpyrrolidone, polyacrylic resin, polyvinyl alcohol, polyamino acids, polycarbonate, polylactic acid, poly(lactic-co-glycolic) acid, and polylactic acid-polyethylene glycol block copolymer.

In some embodiments, the hexahydro-β-acid compound included in the feed composition is provided as a coated substance with a feed-acceptable adjuvant, wherein the feed-acceptable adjuvant is selected from fatty acids.

Furthermore, the fatty acids include but are not limited to lauric acid, myristic acid, palmitic acid, and stearic acid.

In some embodiments, the fatty acid is preferably palmitic acid or stearic acid.

In some embodiments, the hexahydro-β-acid compound included in the feed composition is provided as a coated substance with a feed-acceptable adjuvant, wherein the feed-acceptable adjuvant is selected from fatty glycerides.

Furthermore, the fatty glycerides are monoglycerides of fatty acids, which include but are not limited to glyceryl monolaurate, glyceryl monomyristate, glyceryl monopalmitate, and glyceryl monostearate.

In some embodiments, the monoglyceride is preferably glyceryl monopalmitate or glyceryl monostearate.

In some embodiments, the hexahydro-β-acid compound included in the feed composition is provided as a coated substance with a feed-acceptable adjuvant, wherein the feed-acceptable adjuvant is selected from triglycerides of fatty acids.

Furthermore, the triglycerides of fatty acids include but are not limited to glyceryl trilaurate, glyceryl trimyristate, glyceryl tripalmitate, and glyceryl tristearate.

In some embodiments, the triglyceride is preferably glyceryl tripalmitate or glyceryl tristearate.

In some embodiments, the hexahydro-β-acid compound included in the feed composition is provided as a coated substance with a feed-acceptable adjuvant, wherein the feed-acceptable adjuvant is selected from fatty alcohols.

Furthermore, the fatty alcohols include but are not limited to lauryl alcohol, myristyl alcohol, palmityl alcohol, and stearyl alcohol.

In some embodiment, the fatty alcohol is preferably palmityl alcohol or stearyl alcohol.

In some embodiments, the hexahydro-β-acid compound included in the feed composition is provided as a coated substance with a feed-acceptable adjuvant, wherein the feed-acceptable adjuvant is selected from proteins.

Furthermore, the proteins include but are not limited to whey protein, casein, bovine serum albumin, ovalbumin, and gelatin.

In some embodiment, the protein is preferably gelatin.

In some embodiments, the hexahydro-β-acid compound included in the feed composition is provided as a coated substance with a feed-acceptable adjuvant, wherein the feed-acceptable adjuvant is a combination of gelatin and sodium alginate.

In some embodiments, the hexahydro-β-acid compound included in the feed composition is provided as a coated substance with a feed-acceptable adjuvant, wherein the feed-acceptable adjuvant is starch.

Furthermore, the starch includes but is not limited to high-amylose corn starch, amylose, porous starch, hyperbranched corn starch, potato starch, rice starch, and chinquapin amylose.

In one embodiment, the hexahydro-β-acid compound included in the feed composition is provided as a coated substance with high-amylose corn starch or amylose.

In some embodiments, the hexahydro-β-acid compound included in the feed composition is provided as a coated substance with a feed-acceptable adjuvant, wherein the feed-acceptable adjuvant comprises starch and the other above-mentioned natural polymer materials.

Furthermore, the starch includes but is not limited to high-amylose corn starch, amylose, porous starch, hyperbranched corn starch, potato starch, rice starch, and chinquapin amylose, while the other natural polymer materials is preferably sodium alginate.

In one embodiment, the hexahydro-β-acid compound included in the feed composition is provided as a coated substance with porous starch and sodium alginate.

In some embodiments, the hexahydro-β-acid compound included in the feed composition is provided as a coated substance with a feed-acceptable adjuvant, wherein the feed-acceptable adjuvant is a combination of a semi-synthetic polymer material and another polymer material.

Furthermore, the semi-synthetic polymer material is preferably ethyl cellulose, and the other polymer material is selected from the group of gelatin, polyvinylpyrrolidone, and salts of carboxymethyl cellulose.

In one specific embodiment, the hexahydro-β-acid compound included in the feed composition is provided as a coated substance with a combination of methyl cellulose and gelatin.

In some embodiments, the above feed composition further comprises an additional animal feed additive and/or an animal feed raw material.

The animal feed additive is a nutritive feed additive, a general feed additive, or a medicinal feed additive.

Nutritive feed additives refer to substances, in small or trace amounts, that are added to a formula feed for balancing feed nutrients, improving feed utilization, and exhibiting direct nutritional effects on animals, which include but are not limited to amino acids, amino acid salts and their analogs, vitamins and vitamin-like substances, mineral elements and their complexes (chelates), microbial enzyme preparations, or non-protein nitrogen.

General feed additives, also called non-nutritive additives, refer to non-nutritive substances added into the feed to improve feed utilization, to ensure feed quality and properties and beneficial to animal health or metabolism, which include but are not limited to growth promoters, vermifuges, flavorings, attractants, feed conditioners, feed modifiers, feed storage agents, and Chinese herbal medicine additives.

In some embodiments, the additional feed additive included in the feed composition is selected from a group of nutritive feed additives, general feed additives, medicinal feed additives and combinations thereof.

Further specifically, the non-nutritive additives are growth promoters, including but not limited to butyric acid, calcium butyrate, sodium butyrate, tannic acid, p-thymol, p-thymol esters, p-thymol salts, 2-hydroxybenzoic acid, benzoic acid or calcium benzoate, zinc oxide, zinc sulfate, and zinc chloride.

In one embodiment, the non-nutritive additive is calcium butyrate.

In another embodiment, the non-nutritive additive is tannic acid.

Further specifically, medicinal feed additives include but are not limited to premixed veterinary drugs with carrier or diluent, which are capable of preventing animal diseases or promoting animal growth and can be presented in feeds for a long-term use.

Further specifically, the medicinal feed additives are feed antibiotics, including but not limited to polymyxin, salinomycin, avilamycin, bacitracin, virginiamycin, nasitide, flavomycin, enramycin, kitasamycin, olaquindox, oxytetracycline, or chlortetracycline.

In some embodiments, the animal feed raw materials are grains and their processed products, oilseeds and their processed products, legumes and their processed products, tubers/tuberous roots and their processed products, other seeds and fruits and their processed products, forages/roughages and their processed products, other plants/algae and their processed products, dairy products and their by-products, terrestrial animal products and their by-products, fish/other aquatic organisms and their by-products, minerals, microbial fermentation products and by-products, other feed raw materials.

Use of Feed Compositions

The present application involves the use of the above-mentioned stable feed composition, wherein the feed composition comprises an optional feed-acceptable adjuvant, and at least one compound selected from hexahydro-β-acid compounds represented by formula (I) and feed-acceptable salts thereof.

In some embodiments, the above-mentioned stable feed composition, wherein the feed composition comprises an optional feed-acceptable adjuvant, and at least one compound selected from hexahydro-β-acid compounds represented by formula (I) and feed-acceptable salts thereof, is used in the preparation of animal feed additives.

Furthermore, the animal feed additives are feed additives for improving animal production performance, which include but are not limited to livestock feed additives, poultry feed additives, aquatic animal feed additives, and pet feed additives.

Specifically, the above-mentioned stable feed composition, wherein the feed composition comprises an optional feed-acceptable adjuvant, and at least one compound selected from hexahydro-β-acid compounds represented by formula (I) and feed-acceptable salts thereof, is used in the preparation of feed additives for livestock, wherein the livestock include but are not limited to pigs, cattle, sheep, horses, rabbits, and minks, of various growth stages.

Specifically, the above-mentioned stable feed composition, wherein the feed composition comprises an optional feed-acceptable adjuvant, and at least one compound selected from hexahydro-β-acid compounds represented by formula (I) and feed-acceptable salts thereof, is used in the preparation of feed additives for poultry, wherein the poultry include but are not limited to chickens, ducks, geese, and pigeons, of various growth stages.

Specifically, the above-mentioned stable feed composition, wherein the feed composition comprises an optional feed-acceptable adjuvant, and at least one compound selected from hexahydro-β-acid compounds represented by formula (I) and feed-acceptable salts thereof, is used in the preparation of feed additives for aquatic animals, wherein the aquatic animals include but are not limited to fish, shrimps, crabs, soft-shelled turtles, and eels, of various growth stages.

Specifically, the above-mentioned stable feed composition, wherein the feed composition comprises an optional feed-acceptable adjuvant, and at least one compound selected from hexahydro-β-acid compounds represented by formula (I) and feed-acceptable salts thereof, is used in the preparation of feed additives for pets, wherein the pets include but are not limited to farm-raised dogs or cats.

In some embodiments, the animal feed additives, prepared from the above-mentioned stable feed composition comprising an optional feed-acceptable adjuvant, and at least one compound selected from hexahydro-β-acid compounds represented by formula (I) and feed-acceptable salts thereof, are premixes, multi-premixes, aqueous solutions, or granules.

In some embodiments, the above-mentioned stable feed composition, wherein the feed composition comprises an optional feed-acceptable adjuvant, and at least one compound selected from the group consisting of hexahydro-β-acid compounds represented by formula (I) and feed-acceptable salts thereof, is used in the preparation of animal feeds.

The feeds involved in the present application refer to products that are industrially processed and manufactured for animal consumption.

The animal feeds, prepared from the above-mentioned stable feed composition comprising an optional feed-acceptable adjuvant, and at least one compound selected from hexahydro-β-acid compounds represented by formula (I) and feed-acceptable salts thereof, are livestock feeds, poultry feeds, aquatic animal feeds, or pet feeds.

Specifically, the above-mentioned stable feed composition, wherein the feed composition comprises an optional feed-acceptable adjuvant, and at least one compound selected from hexahydro-β-acid compounds represented by formula (I) and feed-acceptable salts thereof, is used in the preparation of feeds for livestock, wherein the livestock include but are not limited to pigs, cattle, sheep, horses, rabbits, and minks, of various growth stages.

Specifically, the above-mentioned stable feed composition, wherein the feed composition comprises an optional feed-acceptable adjuvant and at least one compound selected from hexahydro-β-acid compounds represented by formula (I) and feed-acceptable salts thereof, is used in the preparation of feeds for poultry, wherein the poultry include but are not limited to chickens, ducks, geese, and pigeons, of various growth stages.

Specifically, the above-mentioned stable feed composition, wherein the feed composition comprises an optional feed-acceptable adjuvant, and at least one compound selected from hexahydro-β-acid compounds represented by formula (I) and feed-acceptable salts thereof, is used in the preparation of feeds for aquatic animals, wherein the aquatic animals include but are not limited to fish, shrimps, crabs, soft-shelled turtles, and eels, of various growth stages.

Specifically, the above-mentioned stable feed composition, wherein the feed composition comprises an optional feed-acceptable adjuvant, and at least one compound selected from hexahydro-β-acid compounds represented by formula (I) and feed-acceptable salts thereof, is used in the preparation of feeds for pets, wherein the pets include but are not limited to farm-raised dogs or cats.

In some embodiments, the animal feeds, prepared from the above-mentioned stable feed composition comprising an optional feed-acceptable adjuvant, and at least one compound selected from the group consisting of hexahydro-β-acid compounds represented by formula (I) and feed-acceptable salts thereof, are single feeds, concentrated feeds, formula feeds, multi-premixes, or concentrate supplements.

Specifically, the compound feeds are complete formula feeds.

Methods for Improving Production Performance of Farmed Animals

In some feeding embodiments, farmers feed animals with feeds mixed with the above-mentioned stable feed composition or the animal feed additive prepared from the feed composition, wherein the feed composition comprises an optional feed-acceptable adjuvant, and at least one compound selected from hexahydro-β-acid compounds represented by formula (I) and feed-acceptable salts thereof. The production performance of the animals can be significantly improved.

Optionally, the feed composition is a feed additive premix, a feed additive multi-premix, a granule, or an aqueous solution, and fed to the animals in combination with feed.

In one embodiment, the feed composition is a feed additive premix.

In one embodiment, the feed composition is a feed additive multi-premixe.

In some embodiments, the feed additives is a premix, a multi-premix, a granule, or an aqueous solution, and fed to animals in combination with animal feed.

The animals are livestock, poultry, aquatic animals, or pets.

Specifically, the livestock include but are not limited to pigs, cattle, sheep, horses, rabbits, and minks, of various growth stages; the poultry include but are not limited to chickens, ducks, geese, and pigeons, of various growth stages; the aquatic animals include but are not limited to fish, shrimps, crabs, soft-shelled turtles, and eels, of various growth stages; the pets include but are not limited to farm-raised dogs or cats.

In one embodiment, farmers feed weaned pigs with feed mixed with the feed additive comprising the hexahydro-β-acid compounds, the racemate thereof, the stereoisomer thereof, the geometric isomer thereof, the tautomer thereof, the solvate thereof, or the feed acceptable salt thereof, and each of the average daily weight gain and feed efficiency of the weaned pigs is significantly improved.

In one embodiment, farmers feed broilers with feeds mixed with the above-mentioned stable feed composition or the animal feed additives prepared from the feed composition, wherein the feed composition comprises an optional feed-acceptable adjuvant, and at least one compound selected from hexahydro-β-Acid compounds represented by formula (I) and feed-acceptable salts thereof. The feed efficiency of the broilers is improved while the feed conversion ratio is significantly reduced.

In one embodiment, farmers feed fish with feeds mixed with the above-mentioned stable feed composition or the animal feed additives prepared from the feed composition, wherein the feed composition comprises an optional feed-acceptable adjuvant and at least one compound selected from hexahydro-β-acid compounds represented by formula (I) and feed-acceptable salts thereof.

In one embodiment, farmers feed young dogs with feeds mixed with the above-mentioned stable feed composition or the animal feed additives prepared from the feed composition, wherein the feed composition comprises an optional feed-acceptable adjuvant, and at least one compound selected from hexahydro-β-acid compounds represented by formula (I) and feed-acceptable salts thereof.

In some other feeding embodiments, farmers feed the animals with the feed prepared from the above-mentioned stable feed composition, wherein the composition comprises an optional feed-acceptable adjuvant and at least one compound selected from hexahydro-β-acid compounds represented by formula (I) and feed-acceptable salts thereof. The production performance of animals can be significantly improved.

Optionally, the feed composition is a concentrated feed, a formula feed, a formula premix, or a concentrate supplement, and directly fed to animals as animal feed.

The premix as used herein refer to homogeneous mixture which mainly comprises a nutritive feed additive selected from the group consisting of mineral trace elements, vitamins, microorganisms, amino acids and combinations thereof, and prepared by mixing the nutritive feed additive with the hexahydro-β-acid compounds of the present application or other feed additives, carriers, and (or) diluents according to specific ratios, wherein the nutritive feed additive is presented therein at concentrations sufficient to meet the basic nutritional needs of the animals applied thereto at specific physiological stages. When added into a formula feed, a concentrate supplement, or a drinking water for animal, the premix is presented at concentrations not lower than 0.1% and not higher than 10%.

The concentrated feed as used herein refer to feed mainly prepared by mixing proteins, minerals, and feed additives according to specific ratios.

Formula feed as used herein refer to feed prepared by mixing multiple feed raw materials and feed additives according to specific ratios based on the nutritional needs of farmed animals.

The concentrate supplement as used herein refer to feed prepared by mixing multiple feed raw materials and feed additives according to specific ratios for nutritional supplementation for herbivores.

In one embodiment, the feed composition is a complete formula feed.

The embodiments of the present application will be described in detail below with examples, but those skilled in the art will understand that the following examples are only used to illustrate the present invention and should not be regarded as limiting the scope of the present invention. If specific conditions are not indicated in the examples, they shall be carried out in accordance with the conventional conditions or the conditions recommended by the manufacturer. Where the involved reagents or instruments are presented without manufactures' names, they are all conventional products that can be commercially purchased.

Example A: Semi-Synthesis of Hexahydro-β-Acid Compounds

Those skilled in the art will recognize that other preparation methods of hexahydro-β-acid compounds herein are all considered to be included in this disclosure. For example, the non-exemplified synthesis of the hexahydro-β-acid compounds herein can be carried out by the technology personnel in the art with modified methods, such as appropriate protecting groups, the use of other reagents, or regular modifications of the reaction conditions.

A1: Preparation of β-Acids

To a 5 L beaker were sequentially added 1 kg of hop extract, 3 L of pure water, and 1 L of ethanol, with stirring to let the hop extract dissolved. To the reaction mixture was added dropwise 0.5 L of KOH solution to give pH13, and the resulting reaction mixture was kept standing and filtered to remove insoluble substances. $CO_2$ gas was pumped to the filtrate to give pH8.5, and the resulting mixture was kept standing for 2 hours, and then filtered to collect the crude product.

The above crude product was dissolved in 200 mL of n-hexane, and the resulting organic solution was washed with water (150 mL×3) and then concentrated to give a paste, which was then dissolved in 300 mL of KOH solution at pH12.5. The resulting mixture was washed with n-hexane (200 mL×3), and the organic phase was abandoned. To the resulting water phase was added an acid to give pH8.5 and extracted by n-hexane (200 mL×3). The combined organic phase was dried over anhydrous sodium sulfate, and concentrated by vacuum evaporation to give 400 g of β-acid crystal. HPLC analysis illustrated that the β-acid crystal mainly consisted of colupulone, adlupulone, and lupulone.

A2: Preparation of Hexahydro-β-Acids 50 g of the β-acid crystal was dissolved in 300 mL of 95% ethanol solution, followed by the addition of 1.7 of 10%

Pd/C. The mixture was stirred under hydrogen atmosphere at room temperature overnight. The reaction was monitored by HPLC. The reaction solution was filtered and the filtrate was concentrated to give 46 g of hexahydro-β-acids crystal.

A3: Separation and Purification of the Main Components of Hexahydro-β-Acids

A3.1 Preparation of Hexahydro-Colupulone

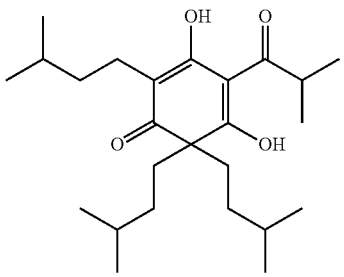 [SMILES: CC(C)CCC1=C(O)C(C(=O)C(C)C)=C(O)C(CCC(C)C)(CCC(C)C)C1=O]

Hexahydro-β-acids was recrystallized in n-hexane to give hexahydro-colupulone with a purity of 98.6%. Structural characterization data of hexahydro-colupulone was as follows.

$^1$HNMR (500 MHz, DMSO-d6): δ (ppm) 3.94-4.01 (m, 1H), 2.39 (t, 2H), 1.78-1.82 (m, 4H), 1.47-1.51 (m, 1H), 1.28-1.35 (m, 4H), 1.11 (q, 6H), 0.95-1.01 (m, 4H), 0.91 (d, 18H); LC-MS(ESI, pos. ion) m/z: 407 [M+H]$^+$

A3.2: Preparation of Hexahydro-Lupulone

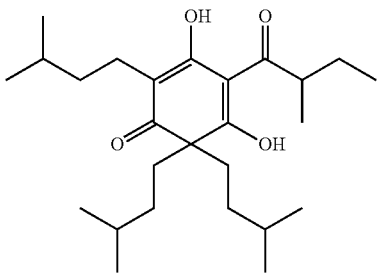 [SMILES: CCC(C)C(=O)C1=C(O)C(CCC(C)C)(CCC(C)C)C(=O)C(CCC(C)C)=C1O]

Hexahydro-lupulone, with a purity of 99.1%, was obtained from hexahydro-β-acids by preparative chromatography. Structural characterization data of hexahydro-lupulone was as follows.

$^1$HNMR (500 MHz, DMSO-d6): δ (ppm) 3.86-3.90 (m, 1H), 2.39 (t, 2H), 1.80-1.83 (m, 4H), 1.59-1.60 (m, 2H), 1.47-1.52 (m, 5H), 1.11 (d, 3H), 0.90-0.96 (m, 7H), 0.86 (d, 18H); LC-MS(ESI, pos. ion) m/z: 421 [M+H]$^+$

A3.3: Preparation of Hexahydro-Adlupulone

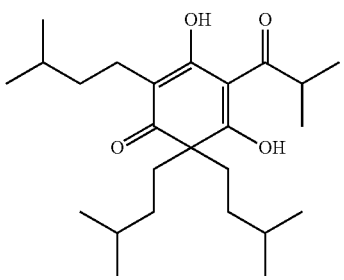 [SMILES: CC(C)CCC1=C(O)C(C(=O)C(C)C)=C(O)C(CCC(C)C)(CCC(C)C)C1=O]

Hexahydro-adlupulone, with a purity of 98.9%, was obtained from hexahydro-β-acids using preparative chromatography. Structural characterization data of hexahydro-adlupulone was as follows.

$^1$HNMR (500 MHz, DMSO-d6): δ (ppm) 2.82-2.84 (m, 2H), 2.37-2.40 (m, 2H), 2.00-2.05 (m, 1H), 1.80-1.88 (m, 4H), 1.77-1.80 (m, 1H), 1.34-1.51 (q, 2H), 1.29-1.33 (m, 2H), 0.90-0.96 (m, 4H), 0.86-0.90 (m, 24H); LC-MS(ESI, pos. ion) m/z: 421 [M+H]$^+$

Example B: Preparation of Coated Hexahydro-β-Acid Compounds

B1: Preparation Method for Coated Substance with Starch 15 g of hexahydro-colupulone or hexahydro-adlupulone was dissolved in 60 mL of ethyl acetate/ethanol mixture (v/v=1:1) to give a solution. 40 g of high-amylose corn starch was added into 190 mL of deionized water with stirring to give a uniform suspension, which was heated to 65° C. to give a paste liquid. The hexahydro-adlupulone solution was slowly added to the high-amylose corn starch paste liquid, which was homogenized in a high-speed homogenizer at 10,000 r/min to give an emulsion. The resulting emulsion was transferred through a pipe to a spray drier having an inlet temperature of 170° C. to produce microcapsules with starch coating for hexahydro-colupulone, which was called coated substance 1, and microcapsules with starch coating for hexahydro-adlupulone, which was called coated substance 2.

B2: Preparation Method for Coated Substance with Gelatin

Appropriate amounts of gelatin and sodium alginate were respectively dissolved in distilled water to give a mixed solution of gelatin and sodium alginate of a specific concentration. An appropriate amount of hexahydro-colupulone or hexahydro-adlupulone was dissolved in an appropriate amount of ethyl acetate/ethanol mixture to give a solution. The solution of hexahydro-colupulone or hexahydro-adlupulone was added to the mixed solution of gelatin and sodium alginate with Tween 80/Span 80 (1:15), and the resulting mixture was heated to 60° C. and placed in a higher-speed shear mixer at 10,000 r/min for 10 minutes. Then the mixture was dispersed in an appropriate amount of water with high-speed stirring, followed by the addition of aqueous solution of 10% acetic acid to give pH4.0-4.2. The mixture was then cooled down to 5° C. with stirring, followed by the addition of CaCl$_2$ solution for gelation. The mixture was kept standing in an ice water bath for 2.5 hours and filtered, and the filter cake was dried in vacuum at 45° C. to give powdery coated substance for hexahydro-colupulone, which was called coated substance 3, and powdery coated substance for hexahydro-adlupulone, which was called coated substance 4.

B3: Preparation Method for Coated Substance with Stearic Acid

Hexahydro-colupulone was evenly mixed with silicon oxide at a ratio of 1:50. Stearic acid was added to a high-speed universal pulverizer, and then the mixture of hexahydro-colupulone and silicon oxide was slowly added to the pulverizer, wherein the ratio of hexahydro-colupulone, silicon oxide and stearic acid was 1:50:10. After thoroughly mixing and pulverization, the mixture was dried in a constant-temperature oven at 80-85° C. After stearic acid was melt down, the mixture was taken out of the oven and cooled to room temperature to give the coated substance of hexahydro-colupulone with stearic acid, called coated substance 5.

Coated substance of hexahydro-adlupulone with stearic acid was produced with the same method and called coated substance 6.

B4: Preparation Method for Coated Substance with Palmitic Acid

Coated substance with palmitic acid was produced with the method of B3, wherein the temperature for mixture drying in the constant-temperature oven was 70-75° C. The coated substance with palmitic acid for hexahydro-colupulone was called coated substance 7, and that for hexahydro-adlupulone was called coated substance 8.

B5: Preparation Method for Coated Substance with Glyceryl Monostearate

Coated substance with glyceryl monostearate was produced with the method of B3, wherein the temperature for mixture drying in the constant-temperature oven was 90-95° C. The coated substance with glyceryl monostearate for hexahydro-colupulone was called coated substance 9, and that for hexahydro-adlupulone was called coated substance 10.

B6: Preparation Method for Coated Substance with Glyceryl Monopalmitate

Coated substance with glyceryl monopalmitate was produced with the method of B3, wherein the temperature for mixture drying in the constant-temperature oven was 85-90° C. The coated substance with glyceryl monopalmitate for hexahydro-colupulone was called coated substance 11, and that for hexahydro-adlupulone was called coated substance 12.

B7: Preparation Method for Coated Substance with Stearyl Alcohol

Coated substance with stearyl alcohol was produced with the method of B3, wherein the temperature for mixture drying in the constant-temperature oven was 70-75° C. The coated substance with stearyl alcohol for hexahydro-colupulone was called coated substance 13, and that for hexahydro-adlupulone was called coated substance 14.

B8: Preparation Method for Coated Substance with Palmityl Alcohol

Coated substance with palmityl alcohol was produced with the method of B3, wherein the temperature for mixture drying in the constant-temperature oven was 60-65° C. The coated substance with palmityl alcohol for hexahydro-colupulone was called coated substance 15, and that for hexahydro-adlupulone was called coated substance 16.

Example C: Preparation of Feed Compositions of Hexahydro-β-Acid Compounds

In the feed compositions of hexahydro-β-acid compounds involved herein, the hexahydro-β-acid compounds, no matter in free form or coated from, are presented at a concentration above or equal to 0.00001%, which can be adjusted according to the feasibility on various animals of various growth stages or products (such as feed additives, feed additive raw materials, feed raw materials) of various properties in the feed industry, and also can be adjusted according to the proportions of other nutritive substances and non-nutritive substances in the feed formulas in order to comply with the feed formulas. The feed compositions herein will be further described below with basic granular premixes as examples; however, any similar formulas, or any changes or increases of formula components which have non-synergistic effect with each other, are deemed consistent with the purpose of the present invention.

Preparation method of feed compositions: Raw material(s) and adjuvant(s) were evenly mixed in a mixer. The resultant mixture and an aqueous solution of 1.3% hydroxypropyl methylcellulose at a ratio of 100:35 were put into a pellet mill where the mixing and cutter process was operated for 3-5 minutes. After pelleting is complete, the product was dried in fluid bed for 30 minutes, and then passed through 16-mesh sieves.

Raw material(s): Hexahydro-β-acid compounds prepared in Example A, and coated substances prepared in Example B Adjuvant(s): Corn starch Formulas: As shown in Table 1

TABLE 1

Formula of granular feed compositions comprising the hexahydro-β-acid compounds

| Product | Raw materials/ Weight | Carrier/ Weight | Adhesive/ Weight |
| --- | --- | --- | --- |
| Composition 1 | Hexahydro-colupulone/1 | 99 | 35 |
| Composition 2 | Hexahydro-adlupulone/1 | 99 | 35 |
| Composition 3 | Hexahydro-colupulone/ Hexahydro-adlupulone (w/w = 1:0.5)/1 | 99 | 35 |
| Composition 4 | Hexahydro-colupulone/ Hexahydro-adlupulone (w/w = 1:0.25)/1 | 99 | 35 |
| Composition 5 | Coated substance 1/1 | 99 | 35 |
| Composition 6 | Coated substance 2/1 | 99 | 35 |
| Composition 7 | Coated substance 3/1 | 99 | 35 |
| Composition 8 | Coated substance 4/1 | 99 | 35 |
| Composition 9 | Coated substance 5/1 | 99 | 35 |
| Composition 10 | Coated substance 6/1 | 99 | 35 |
| Composition 11 | Coated substance 7/1 | 99 | 35 |
| Composition 12 | Coated substance 8/1 | 99 | 35 |
| Composition 13 | Coated substance 9/1 | 99 | 35 |
| Composition 14 | Coated substance 10/1 | 99 | 35 |
| Composition 15 | Coated substance 11/1 | 99 | 35 |
| Composition 16 | Coated substance 12/1 | 99 | 35 |
| Composition 17 | Coated substance 13/1 | 99 | 35 |
| Composition 18 | Coated substance 14/1 | 99 | 35 |
| Composition 19 | Coated substance 15/1 | 99 | 35 |
| Composition 20 | Coated substance 16/1 | 99 | 35 |

Example D: Preparation of Feed Products of Hexahydro-β-Acid Compounds

D1: Preparation of Hog Feed

A feed suitable for hogs ("feed D1"), comprising corn-soybean meal basal diet and hexahydro-colupulone, wherein the concentration of hexahydro-colupulone was 25 ppm according to the formula of a complete formula feed, was a granule feed. The raw materials was pulverized, and then made into granule feed through pelleting process of extruded feed.

D2: Preparation of Hog Feed

A feed suitable for hogs ("feed D2") comprising corn-soybean meal basal diet and hexahydro-adlupulone, wherein the concentration of hexahydro-adlupulone was 25 ppm according to the formula of a complete formula feed, was a granule feed. The raw material was pulverized, and then made into granule feed through preparation technology of pellet-fodder.

D3: Preparation of Hog Feed

A feed suitable for hogs ("feed D3"), comprising corn-soybean meal basal diet and the coated substance of hexahydro-colupulone with high-amylose corn starch, wherein the concentration of hexahydro-colupulone was 25 ppm according to the formula of a complete formula feed, was a granule feed. The raw materials were pulverized, and then made into granule feed through preparation technology of pellet-fodder.

D4: Preparation of Hog Feed

A feed suitable for hogs ("feed D4"), comprising corn-soybean meal basal diet and the coated substance of hexahydro-adlupulone with gelatin, wherein the concentration of hexahydro-adlupulone was 25 ppm according to the formula of a complete formula feed, was a granule feed. The raw materials were pulverized, and then made into granule feed through preparation technology of pellet-fodder.

D5: Preparation of Hog Feed

A feed suitable for hogs ("feed D5"), comprising corn-soybean meal basal diet, hexahydro-colupulone, and hexahydro-adlupulone, wherein the concentrations of hexahydro-colupulone and hexahydro-adlupulone were 17 ppm and 8 ppm respectively according to the formula of a complete formula feed, was a granule feed. The raw materials were pulverized, and then made into granule feed through preparation technology of pellet-fodder.

D6: Preparation of Hog Feed

A feed suitable for hogs ("feed D6"), comprising corn-soybean meal basal diet and the coated form of hexahydro-colupulone with stearic acid (coated substance 5), wherein the concentration of hexahydro-colupulone was 25 ppm according to the formula of a complete formula feed, was a granule feed. The raw materials were pulverized, and then made into granule feed through preparation technology of pellet-fodder.

D7: Preparation of Hog Feed

A feed suitable for hogs ("feed D7"), comprising corn-soybean meal basal diet and the coated form of hexahydro-colupulone with palmitic acid (coated substance 7), wherein the concentration of hexahydro-colupulone was 25 ppm according to the formula of a complete formula feed, was a granule feed. The raw materials were pulverized, and then made into granule feed through preparation technology of pellet-fodder.

D8: Preparation of Hog Feed

A feed suitable for hogs ("feed D8"), comprising corn-soybean meal basal diet and the coated form of hexahydro-colupulone with glyceryl monopalmitate (coated substance 11), wherein the concentration of hexahydro-colupulone was 25 ppm according to the formula of a complete formula feed, was a granule feed. The raw materials were pulverized, and then made into granule feed through preparation technology of pellet-fodder.

D9: Preparation of Hog Feed

A feed suitable for hogs ("feed D9"), comprising corn-soybean meal basal diet and the coated form of hexahydro-colupulone with stearyl alcohol (coated substance 13), wherein the concentration of hexahydro-colupulone was 25 ppm according to the formula of a complete formula feed, was a granule feed. The raw materials were pulverized, and then made into granule feed through preparation technology of pellet-fodder.

Example E: Study on Chemical Stability of Hexahydro-β-Acid Compounds

Chemical stability of the hexahydro-β-acid compounds and 1 wt % premixes thereof at 60° C., and chemical stability of the feeds thereof at room temperature, were assessed.

E1: Equipment

Stability testing chamber; High Performance Liquid Chromatography System of Waters (HPLC).

E2: Standard Substances

Hexahydro-colupulone; hexahydro-lupulone; hexahydro-adlupulone.

E3: Samples

Hexahydro-colupulone, hexahydro-lupulone, hexahydro-adlupulone, and hexahydro-β-acids prepared in Example A; coated substances prepared in Example B; compositions 1 and 2 prepared in Example C; feeds D1-D9 prepared in Example D.

E4: Reagents

Methanol (chromatographic grade); phosphoric acid (analytical grade).

E5: Experiment

E5.1: Preparation of Standard Solutions 50 mg of standard substance was accurately weighed out and dissolved in an appropriate amount of methanol by ultrasonication. The solution was then transferred to a 50 mL volumetric flask and diluted to volume with methanol to give a stock solution. Working solutions with concentration as 25 ppm, 125 ppm, 250 ppm, 500 ppm, and 1000 ppm were prepared respectively by the dilution of appropriate amount of the stock solution. Between concentration of sample and the response value of HPLC peak area, the linearity was adjusted and detected to give a standard curve.

E5.2: Preparation of Sample Solutions

Appropriate amounts of hexahydro-colupulone, hexahydro-lupulone, hexahydro-adlupulone, hexahydro-β-acids, and the related compositions were accurately weighed out and respectively dissolved in an appropriate amount of methanol by ultrasonication to give solutions of 500 ppm (wherein the 500 ppm was the concentration of hexahydro-β-acids/hexahydro-β-acid compound), and then the resulting solutions were filtered through 0.22 μm filters and then analyzed by HPLC.

Appropriate amounts of the feeds were accurately weighed out and respectively dissolved in an appropriate amount of methanol by ultrasonication to give solutions of 50 ppm, and then the resulting solutions were filtered through 0.22 μm filters and then analyzed by HPLC.

E6: Analysis Conditions

Column: Symmetry C18 column (Waters; 250 mm*4.6 mm, 5 μm)

Mobile phase: 0.02% phosphoric acid:methanol=5:95 (v:v)

Wavelength: 223 nm

Column temperature: 25° C.

Injection volume: 10 μL

Flow rate: 1 mL/min

E7: Experimental Method

Thermal stability testing: The test samples were spread in petri dishes to form thin layers of ≤5 mm and placed in a drug stability testing chambers at 60° C. Samples were taken with 3 replications in parallel for each of test samples on day 5 and day 10 for HPLC analysis. Results were shown in Table 2.

Stability testing at ambient temperature: The samples were placed in a room-temperature environment. Samples were taken on day 5 and day 10 for HPLC analysis, and three replications were taken in parallel for each test sample. Results were shown in Table 2.

TABLE 2

Stability testing of hexahydro-β-acid compounds and the products thereof

| Condition | Sample | Sample | Concentration (%) | | | | |
|---|---|---|---|---|---|---|---|
| | | | Day 5 | Day 10 | Day 30 | Day 60 | Day 90 |
| 60° C. | Hexahydro-β-acid compound | Hexahydro-colupulone | 99.76 | 99.10 | — | — | — |
| | | Hexahydro-lupulone | 99.10 | 92.85 | — | — | — |
| | | Hexahydro-adlupulone | 98.01 | 96.63 | — | — | — |
| | | Coated substance 1 | 99.93 | 99.67 | — | — | — |
| | | Coated substance 2 | 99.58 | 99.36 | — | — | — |
| | | Coated substance 3 | 99.98 | 99.81 | — | — | — |
| | | Coated substance 4 | 99.23 | 99.01 | — | — | — |
| | Hexahydro-β-acids | Hexahydro-colupulone | 96.48 | 90.43 | — | — | — |
| | | Hexahydro-lupulone | 91.97 | 79.62 | — | — | — |
| | | Hexahydro-adlupulone | 91.48 | 82.87 | — | — | — |
| | 1% Premix of Hexahydro-β-acid compound | Hexahydro-colupulone | 99.39 | 97.39 | — | — | — |
| | | Hexahydro-lupulone | 92.37 | 91.21 | — | — | — |
| | | Hexahydro-adlupulone | 97.24 | 95.68 | — | — | — |
| | 1% Premix of Hexahydro-β-acids | Hexahydro-colupulone | 97.02 | 97.56 | — | — | — |
| | | Hexahydro-lupulone | 89.92 | 87.62 | — | — | — |
| | | Hexahydro-adlupulone | 88.97 | 88.63 | — | — | — |
| Room temperature | Feed comprising 25 ppm of hexahydro-β-acid compound | Feed D1 | 98.28 | 96.93 | 93.07 | 77.54 | 68.28 |
| | | Hexahydro-lupulone | 17.78 | 4.96 | — | — | — |
| | | Feed D2 | 95.89 | 94.83 | 83.14 | 72.92 | 65.81 |
| | | Feed D3 | 99.74 | 99.31 | 98.62 | 98.03 | 97.19 |
| | | Feed D4 | 99.82 | 98.29 | 97.85 | 97.43 | 96.97 |
| | | Feed D6 | 99.93 | 99.37 | 99.05 | 98.55 | 97.46 |
| | | Feed D7 | 99.32 | 99.11 | 98.97 | 98.17 | 97.53 |
| | | Feed D8 | 98.79 | 98.56 | 98.33 | 97.86 | 97.08 |
| | | Feed D9 | 99.29 | 99.05 | 98.73 | 98.04 | 97.81 |
| | Feed comprising 25 ppm of hexahydro-β-acids | Hexahydro-colupulone | 53.88 | 37.69 | — | — | — |
| | | Hexahydro-lupulone | 63.08 | 0 | — | — | — |
| | | Hexahydro-adlupulone | 60.55 | 0 | — | — | — |

Note:

Concentrations of each component at day 0 were deemed to be 100%.

"—" represents "not detected".

As shown in Table 2, the three main components in the hexahydro-β-acids are hexahydro-colupulone, hexahydro-lupulone, and hexahydro-adlupulone. The stability studies investigated the thermal stability of the hexahydro-β-acid compounds and coated substances thereof, as well as the stability at ambient temperature of the main ingredients in the feeds herein.

In thermal stability testing at 60° C., the hexahydro-β-acids exhibited a decrease of about 10% in the concentration of hexahydro-colupulone therein at day 10, and a decrease of about 20% in the concentration of each of the other two components. When in the form of 1% premix, the hexahydro-β-acids exhibited a decrease of about 2.4% in the concentration of hexahydro-colupulone therein at day 10, and a decrease of about 12% in the concentration of each of the other two components. In addition, the stability at 60° C. of hexahydro-colupulone, hexahydro-lupulone, and hexahydro-adlupulone, and the coated substances and 1% premixes thereof, were investigated respectively. During a 10-day testing period, hexahydro-colupulone, the coated substance 1 and coated substance 3, and the 1% premix thereof, respectively exhibited a degradation ratio of 0.9%, 0.33%, 0.19% and 2.6%; hexahydro-adlupulone, the coated substance 2 and coated substance 4, and the 1% premix thereof, respectively exhibited a degradation ratio of 3.4%, 0.64%, 0.99%, and 4.3%; hexahydro-lupulone, and the 1% premix thereof, respectively exhibited a degradation ratio of 7.2% and 8.8%.

In view of the above, the hexahydro-β-acids as a whole exhibited poor thermal stability; hexahydro-colupulone and hexahydro-adlupulone, and the coated substances and premixes thereof, respectively exhibited a decrease lower than 5%, suggesting that they are relatively more stable. In addition, in the thermal stability testing at 60° C., the coated substances of hexahydro-colupulone and hexahydro-adlupulone were assessed respectively for their stability during a 10-day period; as shown in Table 2, the coated substances herein respectively exhibited a decrease not higher than 1%, and the stability was improved comparing with the free forms of hexahydro-colupulone and hexahydro-adlupulone.

In the stability testing at ambient temperature, the feed comprising hexahydro-β-acids of 25 ppm exhibited a rapid decrease of the concentration of each component, wherein the concentrations of hexahydro-lupulone and hexahydro-adlupulone decreased to 0 at the end, while the concentration of hexahydro-colupulone decreased to 37.69%. In the 10-day period of the stability testing at ambient temperature of the feeds, wherein the feeds comprised 25 ppm of hexahydro-colupulone (feed D1), hexahydro-lupulone, hexahydro-adlupulone (feed D2), the coated substance of hexahydro-colupulone with starch (feed D3), and the coated substance of hexahydro-adlupulone with gelatin (feed D4), the hexahydro-lupulone group exhibited a decrease of 95% of hexahydro-lupulone, the hexahydro-adlupulone group exhibited a decrease of about 5.2% of hexahydro-adlupulone, while the hexahydro-colupulone group exhibited a decrease of about 3.1% of hexahydro-colupulone; and the coated substance of hexahydro-colupulone with starch exhibited a decrease of 0.7% of hexahydro-colupulone, and the coated substance of hexahydro-adlupulone with gelatin exhibited a decrease of about 1.7% of hexahydro-adlupulone. In view of the above, hexahydro-colupulone and hexahydro-adlupulone have an excellent short-term stability during the storage of feeds.

In addition, in the 90-day period of the stability testing at ambient temperature of the feeds, wherein the feeds comprising 25 ppm of hexahydro-colupulone (feed D1), hexahydro-lupulone, hexahydro-adlupulone (feed D2), the coated form of hexahydro-colupulone with starch (feed D3), and the coated form of hexahydro-adlupulone with gelatin (feed D4), the concentration of hexahydro-colupulone in the feed D1 and the concentration of hexahydro-adlupulone in the feed D2 were observed to gradually decrease respectively, wherein the decrease thereof was respectively about 32% and 34% at the end of the 90-day period; the decrease was about 3% in the concentration of hexahydro-colupulone in the coated substance with starch (feed D3) and in the concentration of hexahydro-adlupulone in the coated form with gelatin (feed D4) respectively; in the concentrations of hexahydro-colupulone in the coated forms with stearic acid, palmitic acid, glyceryl monopalmitate, and stearyl alcohol, the decreases were all not higher than 3%. It can be seen that, in the premixes or feeds, the concentration of hexahydro-colupulone and hexahydro-adlupulone, as the component compounds of hexahydro-β-acids and isolated from hexahydro-β-acids, did not change significantly during the short-term stability testing; however, significant degradation of the concentration thereof was still observed in the 90-day long-term stability testing, which is unfavourable to the temporary storage of feeds unused due to various reasons; the non-significant changes of the concentrations of hexahydro-colupulone or hexahydro-adlupulone in the coated substances with different coating materials indicated that the coated substances of hexahydro-colupulone and hexahydro-adlupulone can greatly improve the stability of hexahydro-colupulone and hexahydro-adlupulone, slowing down the degradation thereof and maintaining the effective content thereof.

Example F: Breeding Experiment

Example F1: Effect of Hexahydro-β-Acid Compounds on Production Performance of Hogs 240 67-day-old Duroc×Landrace×Yorkshire cross-bred bacon-type piglets with similar body weight, were randomly divided into 8 groups, with 3 replications per group, 10 piglets per replication and equal amount of males and females. The pig pen and tools were sterilized before the experiment. During the experiment, the piglets were kept in separate regions in the same pig pen under the same feeding and management conditions. The piglets were given ad libitum access to food and water, and feeds were provided twice every day. The groups were control group (group 1) and test groups 2 to 8, wherein piglets of the control group were given basal ration only, those of the test groups 2 to 8 were respectively given basal ration in combination with different additives with 25 ppm of active ingredient thereof, wherein the active ingredient was hexahydro-β-acids, or the hexahydro-β-acid compounds, or the coated substances of the hexahydro-β-acid compounds, as shown in Table 3.

During the entire process, each test group was not given other antioxidants or growth promoters. The experiment lasted for 14 days. On the 14th day, after withdrawing feed (without withdrawing water) for 12 hours, taking each replicate as one unit, the weight of each replication piglets was measured and each of average daily feed intake (ADFI, g/d per piglet), average daily weigh gain (ADG, g/d per piglet), and feed conversion ratio (FCR) was calculated.

Average daily feed intake=(Total weight of provided feed−Weight of remaining feed)/(Number of days×Amount of piglets in each replicate)

Average daily weight gain=(final average body weight−initial average body weight)/number of test days Feed conversion ratio=average daily feed intake/average daily weight gain Results were shown in Table 3.

TABLE 3

Effect of hexahydro-β-acid compounds on production performance of hogs

| Group | Additive | ADFI (g/d per piglet) | ADG (g/d per piglet) | FCR |
|---|---|---|---|---|
| 1 | — | 873 | 358 | 2.437 |
| 2 | Hexahydro-β-acids | 859 | 361 | 2.379 |
| 3 | Hexahydro-colupulone | 894 | 403 | 2.218 |
| 4 | Hexahydro-lupulone | 864 | 358 | 2.413 |
| 5 | Hexahydro-adlupulone | 860 | 368 | 2.340 |
| 6 | Coated substance 1 | 872 | 393 | 2.217 |
| 7 | Coated substance 4 | 885 | 396 | 2.231 |
| 8 | Coated substance 5 | 890 | 402 | 2.215 |
| 9 | Coated substance 7 | 876 | 393 | 2.228 |
| 10 | Coated substance 11 | 883 | 396 | 2.221 |
| 11 | Coated substance 13 | 874 | 394 | 2.219 |
| 12 | Hexahydro-colupulone/hexahydro-adlupulone (1:0.5) | 875 | 380 | 2.301 |

Noted:
In group 12, the additive "hexahydro-colupulone/hexahydro-adlupulone (1:0.5)" refers to the ratio of hexahydro-colupulone to hexahydro-adlupulone in the concentration of 25 ppm.

As shown in Table 3, effect of the test samples on the production performance of piglets was evaluated in terms of three factors: feed intake, weight gain, and feed efficiency. Where the difference in one factor between one test group and the control group was above 5%, the test group is deemed to be changed obviously in that factor.

Specifically, in terms of feed intake, compared with the control group, the test groups 2-12 respectively exhibited a change rate of −1.60%, 2.40%, −1.03%, 1.49%, −0.11%, 1.37%, 1.95%, 0.34%, 1.14%, 0.11%, and 0.23%, and each change of the feed intake was not obvious. In terms of weight gain, compared with the control group, the test groups 2-12 respectively exhibited a change rate of 0.84%, 12.57%, 0, 2.79%, 6.42%, 10.61%, 12.29%, 9.78%, 10.61%, 10.06%, and 6.14%, wherein an obvious increase in average daily weight gain was observed respectively in the groups of hexahydro-colupulone, hexahydro-adlupulone, coated substance 1, and coated substance 4 and group 12. In feed conversion ratio, compared with the control group, the test groups 2-12 respectively exhibited a decrease rate of 2.38%, 8.99%, 0.98%, 3.98%, 6.16%, 8.45%, 9.11%, 8.86%, 8.94%, and 5.58%.

In view of the above, compared with the hexahydro-β-acids, each of hexahydro-colupulone, hexahydro-adlupulone, coated substance 1, coated substance 4, coated substance 5, coated substance 7, coated substance 11, coated substance 13 and the additive of group 12 could improve the animal production performance effectively, wherein hexahydro-colupulone improves obviously the weight gain and feed efficiency of the piglets.

Example F2: Effect of Hexahydro-β-Acid Compounds on Production Performance of Broilers The experiment was conducted with single-factor randomized design. 720 1-day-old yellow broilers with a similar average body weight of 50 g, were randomly divided into 8 groups, with 6 replicates per group, equal amount of males and females and 15 yellow broilers per replicate. The chicken house and tools were sterilized before the experiment. During the experiment, the broilers were kept in separate regions in the same chicken house under the same feeding and management conditions. Basal ration mainly consisted of corn and soybean meal. During the entire process, each group was not given other antioxidants or growth promoters. The groups were control group (group 1) and test groups 2 to 8, wherein the control group was given basal ration only, while the test groups 2 to 8 were respectively given basal ration in combination with the different additives with 25 ppm of the active ingredient thereof, wherein the active ingredient was hexahydro-β-acids, or the hexahydro-β-acid compounds, or the coated substances of the hexahydro-β-acid compounds as shown in Table 4.

The experiment lasted for 30 days. The broilers were given ad libitum access to food and water, and feeds were provided twice every day. At the day when the broilers were 31-day old (after withdrawing feed for 12 hours, without withdrawing water), taking each replicate as one unit, body weight of the broilers was measured, and each of average daily feed intake (ADFI, g/d per broiler), average daily weigh gain (ADG, g/d per broiler), and feed conversion ratio (FCR) was calculated.

Feed conversion ratio (FCR)=average daily feed intake/average daily weight gain

Results were as shown in Table 4.

TABLE 4

Effect of hexahydro-β-acid compounds on production performance of broilers

| Group | Additive | ADFI (g/d per broiler) | ADG (g/d per broiler) | FCR |
|---|---|---|---|---|
| 1 | — | 49.55 | 23.14 | 2.14 |
| 2 | Hexahydro-β-acids | 50.35 | 24.81 | 2.03 |
| 3 | Hexahydro-colupulone | 49.68 | 25.19 | 1.97 |
| 4 | Hexahydro-lupulone | 49.13 | 23.58 | 2.08 |
| 5 | Hexahydro-adlupulone | 50.06 | 24.59 | 2.04 |
| 6 | Coated substance 1 | 48.32 | 24.28 | 1.99 |
| 7 | Coated substance 4 | 49.95 | 25.35 | 1.97 |
| 8 | Hexahydro-colupulone/hexahydro-adlupulone (1:0.25) | 48.86 | 24.43 | 2.00 |

Noted:
In group 8, the additive "hexahydro-colupulone/hexahydro-adlupulone (1:0.25)" refers to the additive herein of 21 ppm comprised 1 part by mass of hexahydro-colupulone and 0.25 part by mass of hexahydro-adlupulone.

As shown in Table 4, effect of the test samples on the production performance of broilers was evaluated in terms of three factors: feed intake, weight gain, and feed efficiency. Where the difference in one factor between one test group and the control group was above 5%, the test group is deemed to be changed obviously in that factor.

Specifically, in terms of feed intake, compared with the control group, the test groups 2-8 respectively exhibited a change rate of 1.61%, 0.26%, −0.85%, 1.03%, −2.48%, 0.81%, and −1.39%. In terms of weight gain, compared with the control group, the test groups 2-8 respectively exhibited a change rate of 7.72%, 8.86%, 1.90%, 6.27%, 4.93%, 9.55%, and 5.57%. In terms of feed conversion ratio, compared with the control group, the test groups 2-8 respectively exhibited a decrease rate of 5.14%, 7.94%, 2.80%, 4.67%, 7.01%, 7.94% and 6.54%.

In view of the above, no significant effect was observed in the feed intake of the broilers with the additive of each test group, while a significant improvement was observed in the average daily weight gain in each test group except the hexahydro-lupulone group. In terms of the decrease in feed conversion ratio, hexahydro-adlupulone and the hexahydro-β-acids were found to produce similar improvement at an identical concentration, while hexahydro-adlupulone were found to be more effective than hexahydro-β-acids; the groups of coated substance 1 and coated substance 4, as well as group 8, also exhibited significant improvement as compared with the control group in terms of feed efficiency.

INDUSTRIAL APPLICABILITY

In the present application, the use of hexahydro-colupulone and/or hexahydro-adlupulone, instead of the hexahydro-β-acids and as a functional component of feed compositions, not only avoids the problem of poor thermal stability and decreased concentration of hexahydro-β-acids during a long-term storage, but also produces more effective improvement in the production performance of animals than hexahydro-β-acids.

What is claimed is:

1. A feed composition, wherein the feed composition comprises an optional feed-acceptable adjuvant; and at least one compound selected from hexahydro-β-acid compounds represented by formula (I) and feed-acceptable salts thereof:

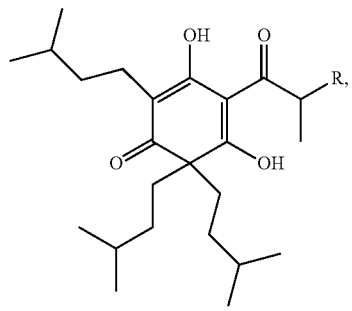
(I)

wherein R is methyl or ethyl, wherein the feed composition is free of hexahydro-lupulone or a salt thereof, wherein the feed composition comprises a hexahydro-β-acid compound represented by formula (i) or a feed-acceptable salt thereof, and a hexahydro-β-acid compound represented by formula (ii) or a feed-acceptable salt thereof:

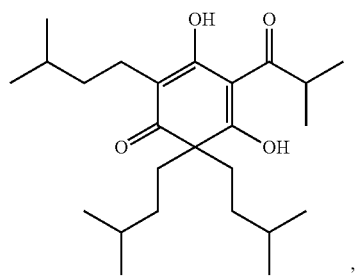
(i)

, and

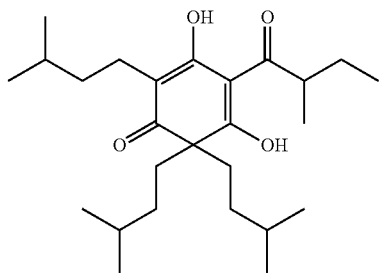
(ii)

, and wherein the weight ratio of the hexahydro-β-acid compound represented by formula (i) or the feed-acceptable salt thereof to the hexahydro-β-acid compound represented by formula (ii) or the feed-acceptable salt thereof is 1:0.01 to 1:0.50; or the weight ratio of the hexahydro-β-acid compound represented by formula (i) or the feed-acceptable salt thereof to the hexahydro-β-acid compound represented by formula (ii) or the feed-acceptable salt thereof is 1:0.25 to 1:0.50.

2. The feed composition according to claim 1, wherein the feed composition further comprises an additional animal feed additive and/or an animal feed raw material.

3. The feed composition according to claim 2, wherein the additional animal feed additive is selected from the group consisting of nutritive feed additives, general feed additives, medicinal feed additives and combinations thereof.

4. The feed composition according to claim 1, wherein the hexahydro-β-acid compound is a coated substance with a feed-acceptable adjuvant.

5. The feed composition according to claim 4, wherein the feed-acceptable adjuvant is selected from the group consisting of natural polymer materials, semi-synthetic polymer materials, synthetic polymer materials and combinations thereof.

6. The feed composition according to claim 5, wherein the feed-acceptable adjuvant is a natural polymer material; and the natural polymer material is selected from the group consisting of starch, alginates, chitosan, proteins, gum arabic and combinations thereof.

7. A method of improving animal production performance, wherein the method comprises:

(i) preparing a feed additive from the feed composition of claim 1; and (ii) administering the feed additive to an animal.

8. A method of improving animal production performance, wherein the method comprises administering a hexahydro-β-acid compound to an animal, wherein the improved production performance of the animal is improved weight gain or feed conversion efficiency compared to an animal not administered with the hexahydro-β-acid compound, and wherein the hexahydro-β-acid compound comprises at least one compound selected from the compounds represented by formula (I) and feed-acceptable salts thereof:

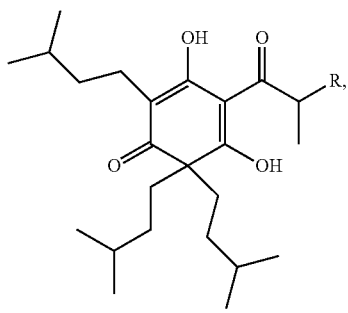

(I)

wherein R is methyl or ethyl;
wherein the hexahydro-β-acid compound comprises a compound represented by formula (i) or a feed-acceptable salt thereof, and a compound represented by formula (ii) or a feed-acceptable salt thereof:

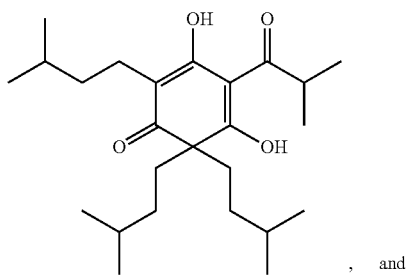

(i)

, and

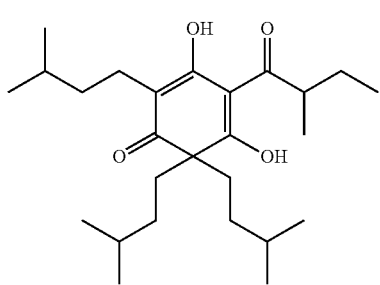

(ii)

;

and wherein the compound represented by formula (i) or the feed-acceptable salt thereof, and the compound represented by formula (ii) or the feed-acceptable salt thereof, are provided respectively at a weight unit of 1 and a weight unit of not high than 0.5; or
the weight ratio of the compound represented by formula (i) or the feed-acceptable salt thereof to the compound represented by formula (ii) or the feed-acceptable salt thereof is 1:0.25 to 1:0.50.

9. The method of claim 8, wherein the hexahydro-β-acid compound is a coated substance with a feed-acceptable adjuvant.

10. The method of claim 8, wherein the hexahydro-β-acid compound represented by formula (i) or the feed-acceptable salt thereof, and the hexahydro-β-acid compound represented by formula (ii) or the feed-acceptable salt thereof, are provided respectively at a weight unit of 1 and a weight unit of not high than 0.5.

11. The method of claim 8, wherein the weight ratio of the hexahydro-β-acid compound represented by formula (i) or the feed-acceptable salt thereof to the hexahydro-β-acid compound represented by formula (ii) or the feed-acceptable salt thereof is 1:0.25 to 1:0.50.

12. A method of improving animal production performance, wherein the method comprises:
(i) preparing an animal feed from the feed composition of claim 1; and
(ii) administering the animal feed to an animal,
wherein the improved production performance of the animal is improved weight gain or feed conversion efficiency compared to an animal not administered with the animal feed.

13. A method of preparing an animal feed from a hexahydro-β-acid compound comprising mixing the hexahydro-β-acid compound with an additional animal feed additive and/or an animal feed raw material, wherein the hexahydro-β-acid compound comprises at least one compound selected from the compounds represented by formula (I) and feed-acceptable salts thereof:

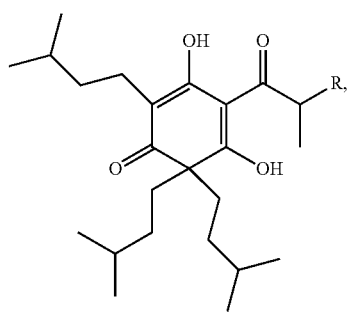

(I)

wherein R is methyl or ethyl;
wherein the hexahydro-β-acid compound comprises a compound represented by formula (i) or a feed-acceptable salt thereof, and a compound represented by formula (ii) or a feed-acceptable salt thereof:

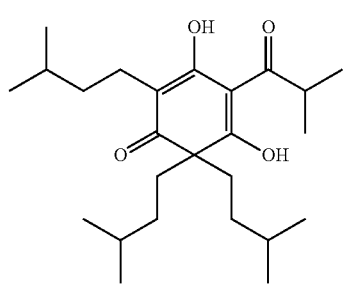

(i)

, and

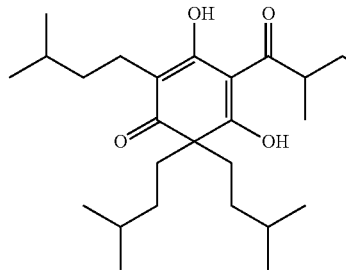

(ii)

;

and wherein the compound represented by formula (i) or the feed-acceptable salt thereof, and the compound represented by formula (ii) or the feed-acceptable salt thereof, are provided respectively at a weight unit of 1 and a weight unit of not high than 0.5; or the weight ratio of the compound represented by formula (i) or the feed-acceptable salt thereof to the compound represented by formula (ii) or the feed-acceptable salt thereof is 1:0.25 to 1:0.50.

14. A method for improving animal production performance, wherein the method comprises: feeding an animal with the feed composition of claim 1, or feeding an animal with a feed comprising the feed composition of claim 1, wherein the improved production performance of the animal is improved weight gain or feed conversion efficiency compared to an animal not administered with the feed composition.

* * * * *